(12) United States Patent
Honda

(10) Patent No.: US 10,117,976 B2
(45) Date of Patent: Nov. 6, 2018

(54) MEDICAL DEVICE

(71) Applicant: TERUMO KABUSHIKI KAISHA, Shibuya-ku, Tokyo (JP)

(72) Inventor: Kei Honda, Hadano (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 104 days.

(21) Appl. No.: 15/068,236

(22) Filed: Mar. 11, 2016

(65) Prior Publication Data
US 2016/0262774 A1 Sep. 15, 2016

(30) Foreign Application Priority Data

Mar. 13, 2015 (JP) ................................. 2015-050994

(51) Int. Cl.
*A61B 17/22* (2006.01)
*A61M 1/00* (2006.01)
*A61B 17/00* (2006.01)
*A61B 90/70* (2016.01)

(52) U.S. Cl.
CPC ........... *A61M 1/0056* (2013.01); *A61B 17/22* (2013.01); *A61B 90/70* (2016.02); *A61B 2017/00473* (2013.01); *A61B 2017/00553* (2013.01); *A61B 2017/22079* (2013.01); *A61B 2217/005* (2013.01)

(58) Field of Classification Search
CPC .......... A61B 2017/22079; A61B 90/70; A61B 2217/005; A61B 2017/00553; A61B 2017/00473; A61M 1/0056
See application file for complete search history.

(56) References Cited

U.S. PATENT DOCUMENTS

| 5,989,266 | A | 11/1999 | Foster | |
| 2002/0176798 | A1* | 11/2002 | Linker | A61M 1/101 422/45 |
| 2003/0135086 | A1* | 7/2003 | Khaw | A61M 1/1024 600/16 |
| 2003/0233143 | A1* | 12/2003 | Gharib | A61F 2/86 623/3.1 |

(Continued)

FOREIGN PATENT DOCUMENTS

| JP | 2001-512355 A | 8/2001 |
| WO | WO 98/36694 A1 | 8/1998 |

*Primary Examiner* — Richard Louis
(74) *Attorney, Agent, or Firm* — Buchanan Ingersoll & Rooney PC

(57) ABSTRACT

A medical device and method are disclosed which can facilitate maintenance work of a filter for capturing a capturing target, and which can improve operability or convenience in the maintenance work. The medical device has an accommodation unit, an impeller holding unit, and a filter. The accommodation unit accommodates a capturing target which is present inside a living body. The impeller holding unit includes an impeller which causes a fluid to flow from a distal side toward a proximal side inside the living body so as to cause the accommodation unit to aspirate the capturing target together with the fluid. Here, the impeller holding unit is configured to be attachable to and detachable from the accommodation unit on a proximal side of the accommodation unit. The filter is arranged in the accommodation unit and/or the impeller holding unit, and captures at last one or more of the capturing target.

18 Claims, 11 Drawing Sheets

(56) References Cited

U.S. PATENT DOCUMENTS

| | | | |
|---|---|---|---|
| 2006/0167539 A1* | 7/2006 | McEwan | A61F 2/01 623/1.35 |
| 2010/0152765 A1* | 6/2010 | Haley | A61F 2/01 606/200 |

\* cited by examiner

MEDICAL DEVICE

CROSS-REFERENCES TO RELATED APPLICATIONS

This application claims priority to Japanese Application No. 2015-050994 filed on Mar. 13, 2015, the entire content of which is incorporated herein by reference.

TECHNICAL FIELD

The present disclosure generally relates to a medical device.

BACKGROUND DISCUSSION

In the related art, treatments have been generally performed in which medical devices such as endoscopes and suction devices are introduced into a biological organ (for example, a body cavity such as an esophagus, airway, intestine, urinary duct, and other organs), and in which these devices are used so as to treat a lesion site appearing in the biological organ, or so as to perform removal of various foreign objects (capturing target) which are present inside the biological organ.

An example of the foreign object can include a calculus formed in the urinary tract. A urinary tract stone is the calculus, which is present in the urinary tract such as the kidney, urinary duct, bladder, and urethra. In case of a urolithiasis, various symptoms are caused to occur due to the urinary tract stone. For example, when the calculus formed inside the kidney moves to the urinary duct, the urinary duct is injured by the calculus, thereby causing pain or hematuria. The calculus occludes the urinary duct, thereby bringing a patient into a transient hydronephrosis state. Consequently, the patient is forced to feel a severe pain (colicky pain) in a range from the waist back to the flank. To remove the calculus is effective means for relieving or treating the symptoms.

In order to remove the calculus, a method has been widely used in which the calculus is picked and extracted by using basket forceps (refer to JP-T-2001-512355). However, it is necessary to pick the calculus one by one and to extract the calculus from a living body. Consequently, the method is a very laborious and inconvenient task.

Here, for example, if a method of collectively removing the calculus is tried in such a way that a filter for use in removing a foreign object inside the blood vessel or the like is diverted for the purpose of efficiently extracting the calculus, the above-described problem may be solved. However, it can be necessary to minimize the filter in view of the filter being introduced into a living body. Consequently, laborious work may be needed in both cleaning and replacement of the filer, thereby causing difficulties in sufficiently carrying out maintenance work.

SUMMARY

A medical device is disclosed, which can improve operability or convenience in maintenance work by facilitating the maintenance work of a filter for capturing a capturing target.

A medical device according to the present disclosure can include an accommodation unit that includes a lumen for accommodating a capturing target present inside a living body, and a distal opening portion and a proximal opening portion which communicate with each other in the lumen, and an impeller holding unit that includes an impeller which causes a fluid to flow from the distal opening portion toward the proximal opening portion inside the living body so as to allow the lumen to aspirate the capturing target together with the fluid, and that is configured to be attachable to and detachable from the accommodation unit on a proximal side of the accommodation unit. A filter for capturing at least one or more of the capturing target is arranged in the accommodation unit and/or the impeller holding unit.

According to a medical device, an accommodation unit and/or an impeller holding unit in which a filter is arranged is separable from the medical device. Accordingly, it is possible to facilitate maintenance work of the filter for capturing a capturing target. Therefore, operability or convenience in the maintenance work can be improved.

A method is disclosed for capturing a target present inside a living body, the method comprising: inserting an accommodation unit into the living body, the accommodation unit including a lumen for accommodating the target present inside the living body, and a distal opening portion and a proximal opening portion which respectively communicate with the lumen; causing a fluid to flow with an impeller holding unit that includes an impeller, which causes the fluid to flow from the distal opening portion toward the proximal opening portion inside the living body so as to allow the lumen to aspirate the target together with the fluid, and wherein the impeller is configured to be attachable to and detachable from the accommodation unit on a proximal side of the accommodation unit; and capturing at least one or more targets with a filter, wherein the filter is arranged in the accommodation unit and/or the impeller holding unit.

BRIEF DESCRIPTION OF THE DRAWINGS

FIGS. 2A and 2B are perspective views illustrating a main unit of the medical device illustrated in FIG. 1, wherein FIG. 2A is a view illustrating a state where an accommodation unit and an impeller holding unit are connected to each other, and FIG. 2B is a view illustrating a state where the accommodation unit and the impeller holding unit are separated from each other.

FIGS. 3A and 3B are perspective sectional views of the main unit of the medical device illustrated in FIG. 1, wherein FIG. 3A is a view taken along line IIIA-IIIA illustrated in FIG. 2A illustrating a state where the accommodation unit and the impeller holding unit are connected to each other, and FIG. 3B is a view in a state where the accommodation unit and the impeller holding unit are separated from each other.

FIGS. 7A, 7B, and 7C are perspective views schematically illustrating a state where a capturing target is collected in the accommodation unit of the medical device illustrated in FIG. 1, wherein FIG. 7A is a view illustrating a state before the capturing target is collected in the accommodation unit, FIG. 7B is a view illustrating a state while the capturing target is collected in the accommodation unit, and FIG. 7C is a view illustrating a state after the capturing target is collected in the accommodation unit.

FIGS. 16A and 16B are perspective views illustrating a first filter and a second filter of the medical device illustrated in FIG. 14, and wherein FIG. 16A is a view illustrating a state where an arrangement of a first holding portion and an arrangement of a second holding portion are caused to coincide with each other in a circumferential direction, and FIG. 16B is a view illustrating a state where the arrangement of the first holding portion and the arrangement of the second holding portion are caused to be different from each other in the circumferential direction.

FIGS. 22A and 22B are perspective sectional views illustrating the medical device illustrated in FIG. 20, wherein FIG. 22A is a view illustrating a state where an arrangement of a second filter is moved along the axial direction, and FIG. 22B is view illustrating a state where an arrangement of the second filter is moved along the circumferential direction.

DETAILED DESCRIPTION

Figure 1:
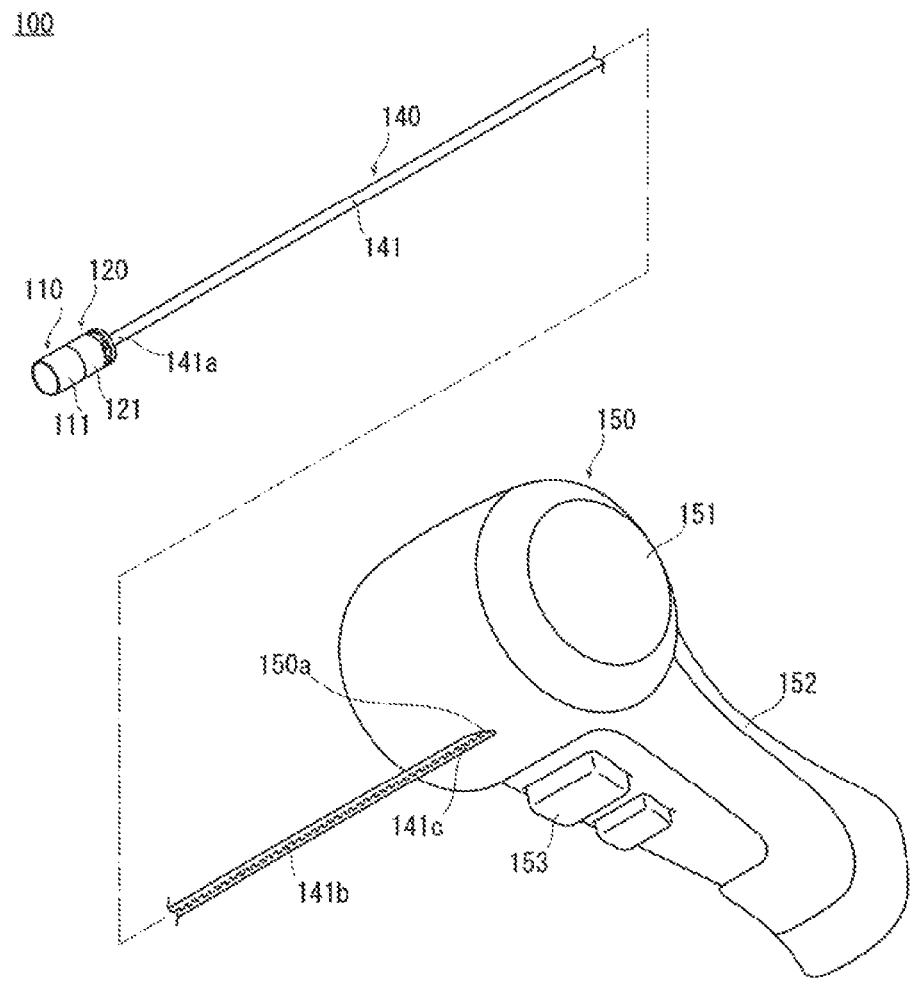
FIG. 1 is a perspective view illustrating a medical device according to a first embodiment.
Figure 2A:
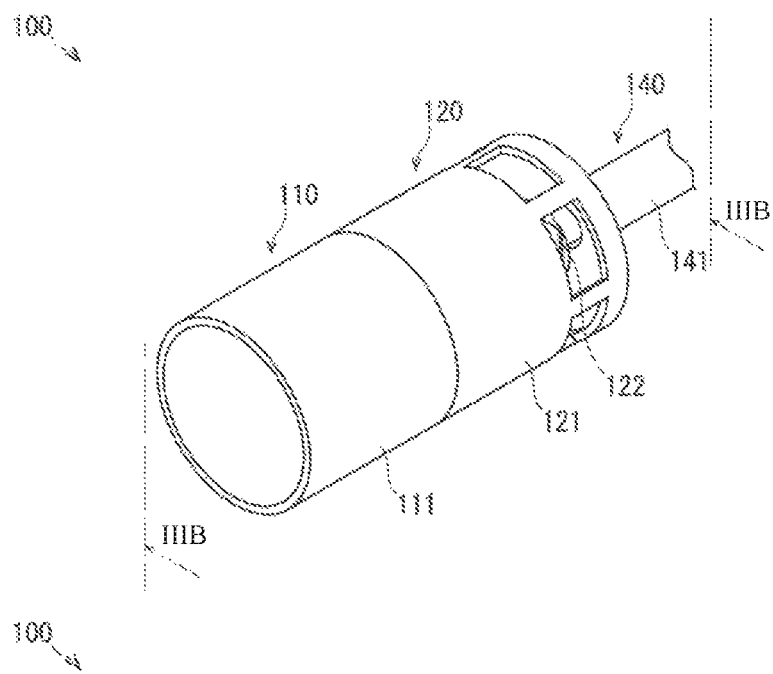
Figure 2B:
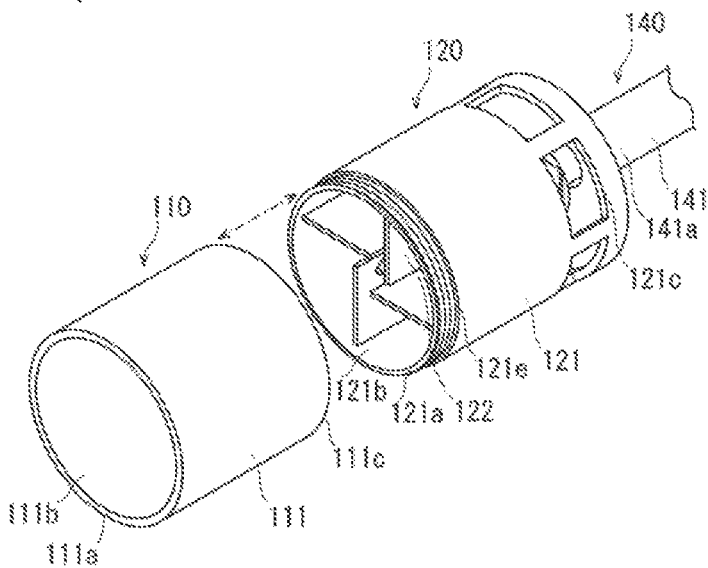

Hereinafter, embodiments of the present disclosure will be described with reference to the drawings. In some cases, dimensional proportions in the drawings may be exaggerated and different from actual proportions for convenience of description. In a medical device 100, an accommodation unit 110 side which is introduced into a living body corresponds to a distal side, and a hand operation unit 150 operated by a user (operator) corresponds to a proximal side.

The medical device 100 according to the first embodiment will be described with reference to FIGS. 1 to 10.

A configuration of the medical device 100 will be described with reference to FIGS. 1 to 4.

The medical device 100 causes a filter to capture a capturing target (for example, a solid calculus K or a semi-solid blood clot B) which is present inside a living body (for example, a urinary duct 630), and then efficiently removes the capturing target. As for the capturing target, the calculus K can include calculus fragments obtained by fragmenting the calculus K present in the, for example, urinary duct 630 by using a laser lithotripsy device, for example, and by relatively decreasing a size thereof. An accommodation unit 110, an impeller holding unit 120, a filter unit 130, an introduction unit 140, and a hand operation unit 150 which configure the medical device 100 will be sequentially described.

As illustrated in FIGS. 1 to 4, the accommodation unit 110 accommodates the capturing target which is present inside the living body such as the urinary duct 630.

The accommodation unit 110 can include a first cylinder 111. The first cylinder 111 is formed in a cylinder shape, and can include a lumen 111b for accommodating the capturing target, which is present, for example, in the urinary duct 630. The first cylinder 111 can include a distal opening portion 111a on a distal side (upstream side along an axial direction) of the lumen 111b, and can include a proximal opening portion 111c on a proximal side (downstream side along the axial direction) of the lumen 111b. For example, the distal opening portion 111a and the proximal opening portion 111c are respectively formed in a circular shape in a cross section orthogonal to the axis.

Figure 4:
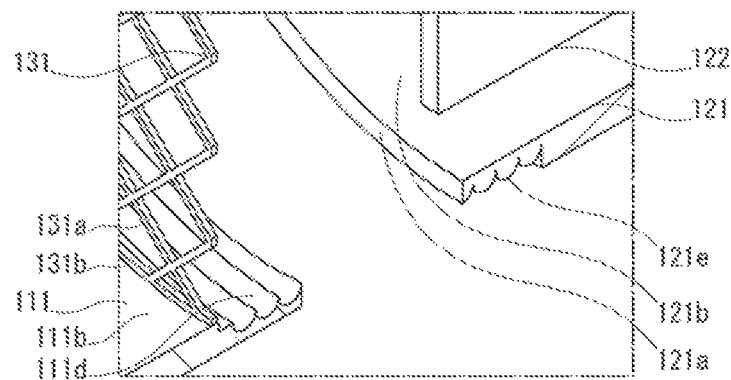
FIG. 4 is a perspective view in which the main unit of the medical device in FIG. 1 is illustrated by enlarging a region 4 illustrated in FIG. 3B.

The first cylinder 111 is joined to a filter 131 of the filter unit 130 on the proximal side (downstream side along the axial direction) of the lumen 111b. As illustrated in FIG. 4, the first cylinder 111 has a screw groove 111d formed on an inner peripheral surface of a proximal side end portion. The screw groove 111d is screwed to a screw thread 121e of a second cylinder 121 of the impeller holding unit 120. That is, the first cylinder 111 is configured to be attachable to and detachable from the second cylinder 121 by means of screwing.

For example, the first cylinder 111 can be configured to include a rigid material, for example, formed of polyolefin, such as acrylic resin, polyvinyl chloride (particularly, rigid polyvinyl chloride), polyethylene, polypropylene, or polybutadiene. In addition, for example, the first cylinder 111 can be configured to include a flexible material, and can be configured to be deformable along a shape of the urinary duct 630. The first cylinder 111 is configured to include a material which is transparent in a visible light region, and can be configured so that a capturing progress of the capturing target is visible from the outside. For example, the first cylinder 111 can be configured to include an X-ray contrast agent. The contrast agent is imaged from the outside by using X-ray fluoroscopy. In this manner, a position of the first cylinder 111 inside the living body can be confirmed.

As illustrated in FIGS. 1 to 4, the impeller holding unit 120 causes a fluid to flow from the distal opening portion 111a toward the proximal opening portion 111c in the urinary duct 630.

The impeller holding unit 120 is configured to be attachable to and detachable from the accommodation unit 110 on the proximal side of the accommodation unit 110. The impeller holding unit 120 can include the second cylinder 121 and an impeller 122. The second cylinder 121 is formed in a cylindrical shape, and accommodates the impeller 122 so as to be rotatable. The second cylinder 121 can include a distal opening portion 121a through which a fluid is caused to flow on a distal side (upstream side along the axial direction) of a lumen 121b. For example, the distal opening portion 121a is formed in a circular shape in a cross section orthogonal to the axis. The second cylinder 121 can include a proximal opening portion 121c through which the fluid is caused to flow (discharged) on a side surface on a proximal side (downstream side along the axial direction) of the lumen 121b. The proximal opening portion 121c is formed at multiple locations at a constant interval along a circumferential direction on the proximal side of the second cylinder 121. The proximal opening portion 121c is formed in a rectangular shape along the circumferential direction of the second cylinder 121.

In the second cylinder 121, a support hole 121f into which an axle portion 122c of the impeller 122 is rotatably inserted for support is formed in the center of the proximal side end portion of the lumen 121b. In the second cylinder 121, a screw thread 121e is formed on an outer peripheral surface in the distal side end portion. The screw thread 121e is screwed to the screw groove 111d of the first cylinder 111 of the accommodation unit 110. The second cylinder 121 is configured to be attachable to and detachable from the first cylinder 111 by means of screwing, but may be configured to be attachable and detachable by employing a configuration other than screwing.

Similarly to the first cylinder 111, the second cylinder 121 can be configured to include a rigid material formed of polyolefin, such as acrylic resin, polyvinyl chloride (particularly, rigid polyvinyl chloride), polyethylene, polypropylene, or polybutadiene. Similar to the first cylinder 111, the second cylinder 121 can be configured to include a material which is transparent in a visible light region, or can be configured to include an X-ray contrast agent.

The impeller 122 causes a fluid to flow from the distal opening portion 111a toward the proximal opening portion 111c, and causes the accommodation unit to aspirate the capturing target together with the fluid. The impeller 122 is rotatably accommodated inside the second cylinder 121. The impeller 122 can include a shaft portion 122a, multiple blade portions 122b, and the axle portion 122c. The impeller 122 configures a propeller-type screw as a whole by using the shaft portion 122a and the multiple blade portions 122b.

Along the axial direction, the shaft portion 122a rotates the blade portion 122b which is joined at multiple locations at a constant interval along the circumferential direction. The shaft portion 122a is a columnar body whose diameter on the distal side (upstream side along the axial direction) is reduced, and has a bullet shape as a whole. The elongated and elastic axle portion 122c is interlocked with an end portion on the proximal side (downstream side along the axial direction) of the blade portion 122b. The axle portion 122c is connected to a motor of a control member 151 of the hand operation unit 150.

The blade portion 122b corresponds to a screw blade portion. If the blade portion 122b is rotated by the shaft portion 122a, a fluid is caused to flow from the distal opening portion 121a of the second cylinder 121 toward the proximal opening portion 121c. The distal opening portion 121a of the second cylinder 121 is interlocked with the proximal opening portion 111c of the first cylinder 111. That is, while the blade portion 122b is rotated, the fluid is caused to flow from the distal opening portion 111a of the first cylinder 111 toward the proximal opening portion 121c of the second cylinder 121.

In the blade portion 122b, the length along the axial direction is longer than the length along the radial direction. In the blade portion 122b, the width along the radial direction is the same as the width along the axial direction, and is formed in a so-called square shape. The blade portion 122b is longitudinally twisted from the distal side to the proximal side based on a rotation axis so that the rotation of the shaft portion 122a enables a fluid to flow. Furthermore, the blade portion 122b is bent radially outward from the rotation axis in a direction opposite to the rotation direction.

Except for the axle portion 122c, for example, the impeller 122 can be configured to include a rigid resin material formed of polyolefin, such as acrylic resin, polyvinyl chloride (particularly, rigid polyvinyl chloride), polyethylene, polypropylene, or polybutadiene. In addition, except for the axle portion 122c, for example, the impeller 122 can be configured to include a metal material, which is a pseudo-elastic alloy (including a super-elastic alloy) such as a Ni—Ti alloy, a shape memory alloy, stainless steel, a cobalt-based alloy, precious metal such as gold and platinum, a tungsten-based alloy, or a carbon-based material (including a piano wire). The axle portion 122c can be configured to include a flexible material.

Figure 3A:
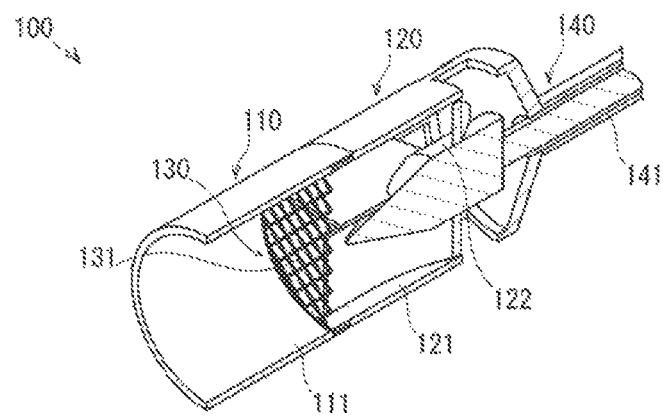
Figure 3B:
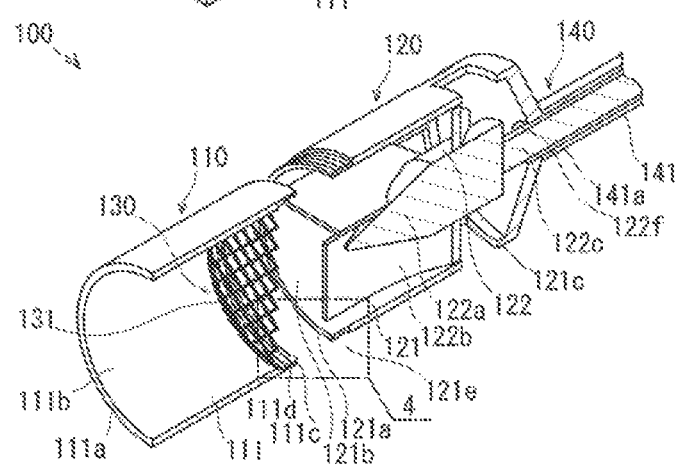

As illustrated in FIGS. 3A, 3B, and 4, the filter unit 130 captures the capturing target in the accommodation unit 110.

The filter unit 130 can include the filter 131. The filter 131 is used in order to capture the capturing target. The filter 131 adopts a configuration which allows a fluid to pass therethrough, and which does not allow the capturing target formed of the solid calculus K or the semi-solid blood clot B, for example. That is, the filter 131 can capture the capturing target by distinguishing the fluid from the capturing target which moves together with the fluid from the distal opening portion 111a of the first cylinder 111 toward the proximal opening portion 111c. The filter 131 is joined to the proximal side of the lumen 111b of the first cylinder 111, but may be detachably attached to the lumen 111b.

The filter 131 can include a holding portion 131a and a frame portion 131b. The holding portion 131a holds the capturing target. In accordance with an exemplary embodiment, the holding portion 131a is formed in a lattice shape. The holding portion 131a is arranged so that a main surface thereof is perpendicular to the axial direction inside the lumen 111b. The frame portion 131b supports the holding portion 131a along the circumferential direction. The frame portion 131b is formed in a ring shape, and is formed integrally with an outer peripheral edge of the holding portion 131a.

For example, the filter 131 can be configured by using a woven fabric formed of woven stuff or knitted fabric, a fibrous material formed of mesh fabric having a predetermined mesh such as non-woven fabric, or a porous film. In accordance with an exemplary embodiment, for example, the mesh fabric has a relatively uniform mesh. Accordingly, the mesh fabric can suitably configure the filter 131. The filter 131 may be configured to include a combination of the above-described multiple materials.

As illustrated in FIGS. 1 to 3B, the introduction unit 140 is used by an operator in order to introduce the accommodation unit 110 and the impeller holding unit 120 into the living body such as the urinary duct 630.

The introduction unit 140 can include an introduction tube 141. The introduction tube 141 is formed in an elongated cylinder shape. A lumen 141b which can rotatably hold the axle portion 122c of the impeller 122 is formed inside the introduction tube 141. A distal end 141a of the introduction tube 141 is joined to the support hole 121f of the second cylinder 121 of the impeller holding unit 120. A proximal end 141c of the introduction tube 141 is connected to a connection port 150a of the hand operation unit 150 so as to be attachable and detachable. The introduction tube 141 is configured to include a flexible material, and can be deformed in accordance with a shape, for example, of the urinary duct 630, or the movement of the flexible scope 700.

As illustrated in FIG. 1, the hand operation unit 150 is operated by an operator in order to adjust a position of the first cylinder 111 introduced into the urinary duct 630, or in order to rotate the impeller 122.

The hand operation unit 150 can include the control member 151, a gripping member 152, and a switch 153. The hand operation unit 150 can include a connection port 150a for connecting the proximal end 141c of the introduction tube 141 of the introduction unit 140 so as to be attachable and detachable. The control member 151 can include a motor for rotating the axle portion 122c of the impeller 122, a control circuit for controlling the motor, and a power source (battery) for supplying power to the motor and the control circuit. A rotary shaft of the motor is interlocked with the axle portion 122c of the impeller 122 so as to be attachable and detachable. If the motor of the control member 151 is rotated, the axle portion 122c of the impeller 122 introduced into the introduction tube 141 is rotatably driven, thereby rotating the impeller 122 inside the second cylinder 121. The gripping member 152 is gripped by an operator. The gripping member 152 internally can store a battery of the control member 151. The switch 153 turns on and off the motor of the control member 151.

A method of using the medical device 100 will be described with reference to FIGS. 5 to 7C.

In the description relating to the method of using the medical device 100, the capturing target will be described as the calculus K, for example.

Figure 6:
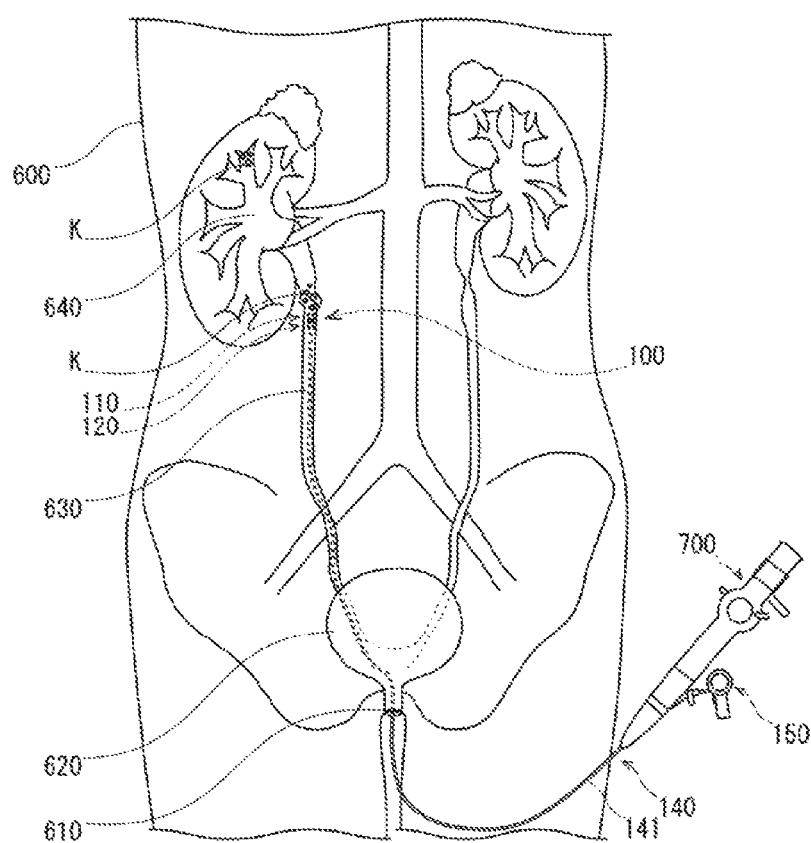
FIG. 6 is a view schematically illustrating a state where the flexible scope on which the medical device illustrated in FIG. 1 is mounted is introduced into a patient's urinary duct.

Hereinafter, a patient 600 who suffers from the urolithiasis will be described by citing a case where the patient 600 has the calculus K present in a region corresponding to a lower urinary duct which is reachable by a rigid scope, and also has the calculus K in a region corresponding to an upper urinary duct which is less likely to be reachable by the rigid scope but is reachable by the flexible scope. In this case of disease, the calculus K in the lower urinary duct is first removed, and then the calculus K in the upper urinary duct is removed. FIG. 6 schematically illustrates a situation when the calculus K in the upper urinary duct is removed after the calculus K in the lower urinary duct is removed.

In order to treat the patient 600 illustrated in FIG. 6, a cystoscope generally used in the urinary system is used so as to introduce a guidewire widely known in the medical field into the urinary duct 630 or a renal pelvis and renal calyx 640 via a urethra 610 and a bladder 620. Next, a rigid pyeloscope (hereinafter, referred to as a rigid scope) is inserted so as to observe an inner wall of the urinary duct 630 or the calculus K inside the urinary duct 630. In this case, the calculus K may be removed by using the rigid scope in combination with basket forceps. In addition, the rigid scope may be used in combination with a fragmenting device, for example, such as a holmum YAG laser so as to fragment the relatively big calculus K, which is less likely to be removed into relatively smaller fragments. Alternatively, the generated calculus fragments may be removed by using the basket forceps. Thereafter, the rigid scope is removed from the inside of the living body.

Next, a ureteral access sheath is introduced into the urinary duct 630 or the renal pelvis and renal calyx 640 via the urethra 610 and the bladder 620 through the guidewire.

The flexible scope 700 is inserted via the ureteral access sheath so as to observe the calculus K. In this case, the guidewire may be removed. When the calculus K has a relatively big size, which is less likely to pass through the ureteral access sheath, the flexible scope 700 is used in combination with the fragmenting device, for example, such as the holmum YAG laser so as to fragment the calculus K into a relatively small size.

Figure 5:
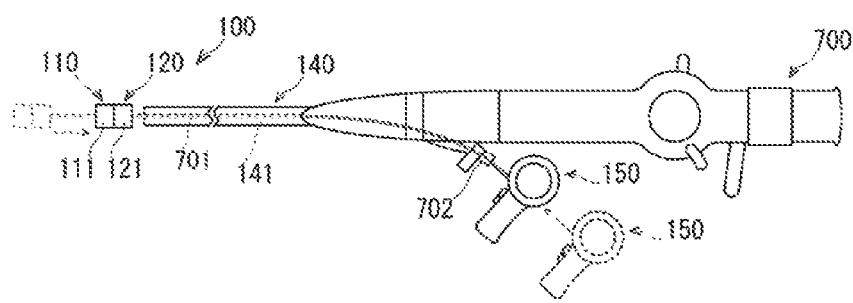
FIG. 5 is a side view schematically illustrating a state where the medical device illustrated in FIG. 1 is mounted on a flexible pyeloscope (hereinafter, referred to as a flexible scope).

Next, the medical device 100 and the flexible scope 700 are assembled to each other. Specifically, as illustrated in FIG. 5, in a state where the introduction tube 141 and the hand operation unit 150 in the medical device 100 are separated from each other, the introduction tube 141 is introduced into a working channel 701 of the flexible scope 700 from the distal side of the flexible scope 700. The proximal side of the introduction tube 141 is extracted from a port 702, and the proximal side of the introduction tube 141 is fitted and attached to the hand operation unit 150.

Next, as illustrated in FIG. 6, the flexible scope 700 having the medical device 100 mounted thereon is caused to pass through the urethra 610 and the bladder 620 of the patient 600 via the ureteral access sheath, and is caused to reach a site having the calculus K present inside the urinary duct 630, for example. Thereafter, the calculus K is collected in the accommodation unit 110 by using the medical device 100.

Figure 7A:
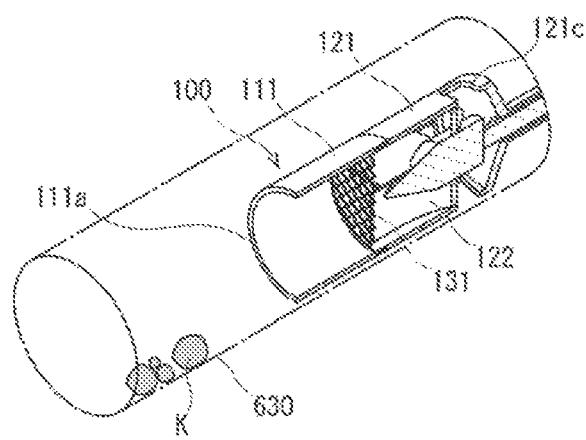
Figure 7B:
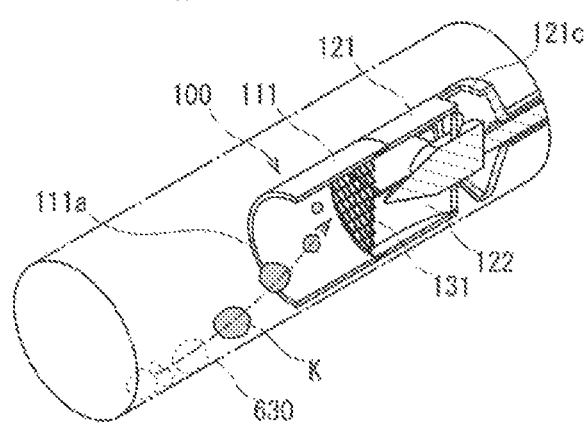
Figure 7C:
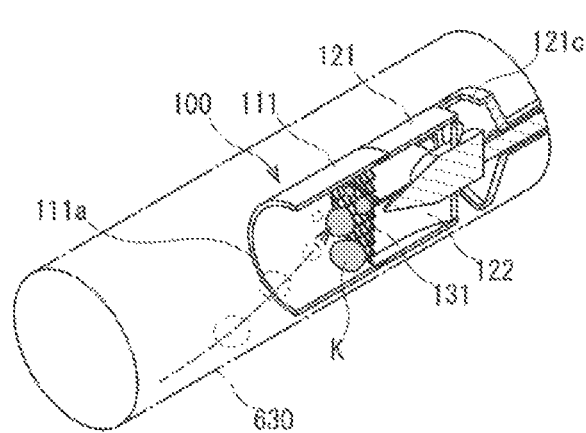

Specifically, as illustrated in FIG. 7A, the first cylinder 111 is caused to move close to the calculus K inside the urinary duct 630 illustrated in FIG. 6. If an operator operates the switch 153 of the hand operation unit 150 so as to rotate the impeller 122, a fluid is caused to flow from the distal opening portion 111a of the first cylinder 111 toward the proximal opening portion 121c of the second cylinder 121. As a result, as illustrated in FIGS. 7B to 7C, the calculus K inside the urinary duct 630 is moved and captured while being attracted to the filter 131 arranged in the first cylinder 111. The calculus K captured by the filter 131 is accommodated in the first cylinder 111.

Next, the first cylinder 111 or the like which collects the calculus K in the first cylinder 111 is conveyed to the outside of the body in a state where the suction force is generated. The first cylinder 111 is detached from the second cylinder 121 and the calculus K inside the first cylinder 111 is removed. Thereafter, the first cylinder 111 is attached to the second cylinder 121 again. Alternatively, a new one of the first cylinder 111 is attached to the second cylinder 121.

Then, the accommodation unit 110 of the medical device 100 is caused to reach the site having the calculus K again. Thereafter, the calculus K is repeatedly aspirated into the first cylinder 111, and is repeatedly removed outside the body. Furthermore, in order to change a position of (reposition) the calculus K, the medical device 100 may be controlled so that the calculus K is aspirated into the first cylinder 111 in a renal calyx located inside the renal pelvis and renal calyx, and so that the rotation of the motor is minimized or stopped in the other renal calyx. In this manner, the calculus K may be released from the first cylinder 111. In this case, an operation may be performed so as to discharge the calculus K from the first cylinder 111 by reversely rotating the motor.

The medical device 100 may be used together with the rigid scope. That is, instead of the basket forceps, the rigid scope may be used for observing, fragmenting, and extracting operations which are performed before the extracting operation is performed by using the flexible scope 700.

Next, the guidewire is introduced into the urinary duct 630 or the renal pelvis and renal calyx 640 via the urethra 610 and the bladder 620. This operation may be performed via the ureteral access sheath. Furthermore, a ureteral stent for upper urinary duct indwelling is caused to indwell while covering the guide wire, and thereafter the guidewire is removed. The ureteral stent corresponds to transient ureteral obstruction or the like after operation. After predetermined days elapse, the ureteral stent is removed.

Whether to use the ureteral access sheath or not is determined by an operator in view of conditions of the urinary duct 630 or the calculus K. That is, without using the ureteral access sheath, observing, fragmenting, and extracting operation may be performed by using the flexible scope 700. Even in this case, the medical device 100 may be used together with the flexible scope 700.

The manual skills described with reference to FIGS. 5 to 7C are mainly as follows. According to a method of removing the capturing target captured by the medical device 100 introduced into the living body of the patient 600, the medical device 100 is introduced into the living body, and the filter 131 captures the capturing target which is moved together with the fluid by causing the fluid to flow inside the living body. Thereafter, the medical device 100 is extracted from the living body, and the capturing target is removed.

A configuration of a cleaning tool 800 for cleaning the medical device 100 will be described with reference to FIGS. 8 and 9.

The cleaning tool 800 can include a holding member 801, a hook member 802, an interlocking member 803, and an operation member 804.

The holding member 801 integrally holds each configuration member of the cleaning tool. As illustrated in FIG. 9, the holding member 801 can include a main body 801*a*, a guiding portion 801*b*, and a support portion 801*c*. As illustrated in FIG. 9, the main body 801*a* has a columnar shape. The main body 801*a* is interlocked with the guiding portion 801*b* on one surface side, and is interlocked with the support portion 801*c* on the other surface side. The main body 801*a* has a through-hole formed in the central portion along the axial direction, and rotatably supports the interlocking member 803. As illustrated in FIG. 9, the guiding portion 801*b* of the holding member 801 guides the hook member 802 so as not to come into contact with the first cylinder 111. The guiding portion 801*b* is formed in a substantially L-shape. That is, the guiding portion 801*b* is formed in a shape, which is laterally cut out into an arcuate shape. As illustrated in FIG. 9, the support portion 801*c* of the holding member 801 supports the operation member 804. The support portion 801*c* is formed in a plate shape. The support portion 801*c* together with the operation member 804 is pinched by an operator. The support portion 801*c* exposes the operation member 804 outward in a state where the operator does not press down the operation member 804. The support portion 801*c* internally stores the operation member 804 in a state where the operator presses down the operation member 804.

The hook member 802 rakes out the capturing target from the accommodation unit 110 of the medical device 100. As illustrated in FIG. 9, the hook member 802 protrudes from the main body 801*a*, and is formed in an elongated and substantially triangular shape. The hook member 802 brings a hook portion 802*a* on the distal side into contact with the capturing target so as to rake out the capturing target. The hook member 802 interlocks a gear portion 802*b* formed in a gear shape on the proximal side with a first gear portion 803*b* of the interlocking member 803. The gear portion 802*b* of the hook member 802 is rotatably accommodated in the guiding portion 801*b* of the holding member 801. The hook member 802 is formed to have a length which helps prevent the hook member 802 from coming into contact with the filter 131 arranged in the first cylinder 111, when the main body 801*a* of the holding member 801 is brought into contact with the first cylinder 111 of the medical device 100.

The interlocking member 803 interlocks an operation of the operation member 804 with the hook member 802. As illustrated in FIG. 9, the interlocking member 803 is formed in a rod shape. The interlocking member 803 can include a rotating portion 803*a* formed to be rotatable in the center of the interlocking member 803. The rotating portion 803*a* is arranged in the main body 801*a* of the holding member 801. The interlocking member 803 interlocks the first gear portion 803*b* formed in a gear shape on one end side thereof with the gear portion 802*b* of the hook member 802. The interlocking member 803 interlocks a second gear portion 803*c* formed in a gear shape on the other end side thereof with a gear portion 804*b* of the operation member 804.

The operation member 804 is used in operating the hook member 802. As illustrated in FIG. 9, the operation member 804 protrudes from the main body 801*a*, and is formed in a trapezoidal shape, which is gradually widened. The operation member 804 interlocks the gear portion 804*b* formed in a gear shape on one end side thereof with the second gear portion 803*c* of the interlocking member 803. The gear portion 804*b* of the operation member 804 is rotatably accommodated in the support portion 801*c* of the holding member 801. If an operator presses down a pressing-down portion 804*a* on the other end side of the operation member 804, the hook member 802 is driven via the interlocking member 803, and is rotated in the clockwise direction in FIG. 9.

A method of using the cleaning tool 800 for cleaning the medical device 100 will be described with reference to FIG. 10.

Figure 8:
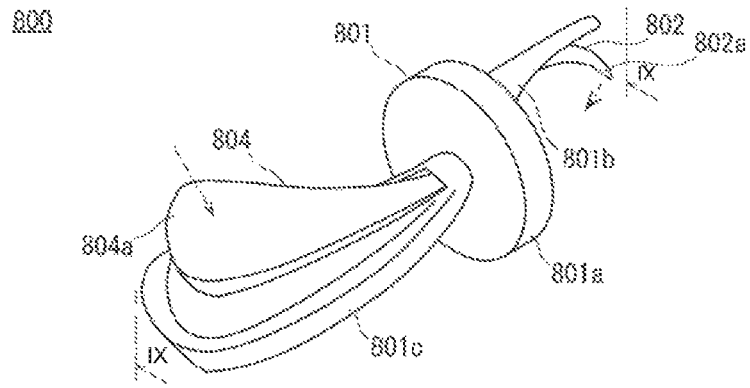
FIG. 8 is a perspective view illustrating a cleaning tool of the medical device illustrated in FIG. 1.
Figure 10:
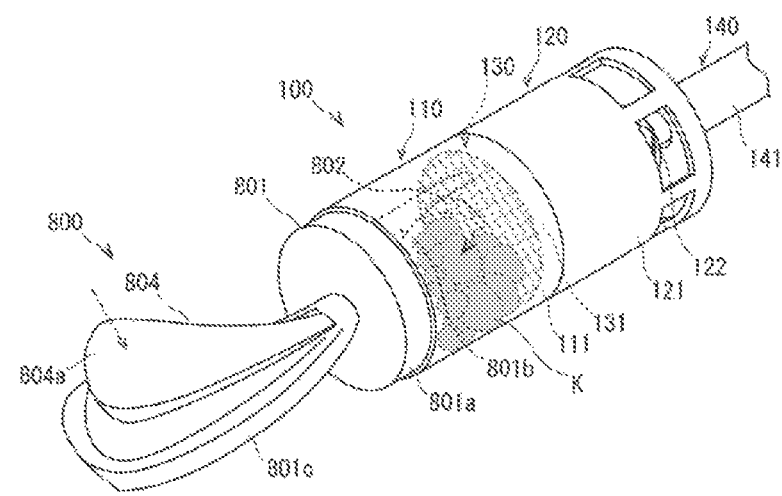
FIG. 10 is a perspective view schematically illustrating a state where a calculus K is extracted from the accommodation unit of the medical device by using the cleaning tool illustrated in FIG. 8.

FIG. 10 is a perspective view schematically illustrating a state where the calculus K is extracted from the accommodation unit 110 of the medical device 100 by using the cleaning tool 800 illustrated in FIG. 8.

As illustrated in FIG. 10, an operator inserts the guiding portion 801*b* of the holding member 801 of the cleaning tool 800 into the first cylinder 111 of the medical device 100. In the above-described state, the operator brings the main body 801*a* of the holding member 801 of the cleaning tool 800 into contact with the first cylinder 111 of the medical device 100. Next, the operator presses down the operation member 804 in a state where the operator pinches the pressing-down portion 804*a* of the operation member 804 and the support portion 801*c* of the holding member 801.

Figure 9:
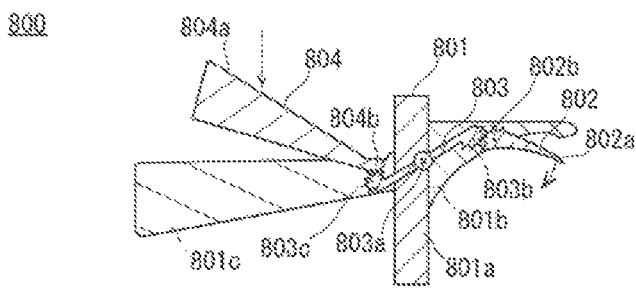
FIG. 9 is a side view in which the cleaning tool in FIG. 8 is illustrated by using a cross section taken along line IX-IX illustrated in FIG. 8.

As a result, the operation member 804 is rotated around the gear portion 804*b* serving as the central axis in the counterclockwise direction illustrated in FIG. 9. In response to the rotation of the operation member 804, the interlocking member 803 is rotated around the rotating portion 803*a* serving as the central axis in the counterclockwise direction illustrated in FIG. 9. In response to the rotation of the interlocking member 803, the hook member 802 is rotated around the gear portion 802*b* serving as the central axis in the clockwise direction illustrated in FIG. 9.

Through these operations, the operator removes the capturing target from the accommodation unit 110 of the medical device 100 by using the cleaning tool 800 as illustrated in FIG. 10. While the operator presses the cleaning tool 800 against the first cylinder 111 so as to rotate, the operator can remove the capturing target.

As described above, according to the medical device 100 of the first embodiment, the following configurations provide an operation effect.

According to the medical device 100, the accommodation unit 110 and/or the impeller holding unit 120 in which the filter 131 is arranged is separable from the medical device 100. Accordingly, it is possible to facilitate maintenance work of the filter 131 for capturing the capturing target. Therefore, operability or convenience in the maintenance work can be improved.

In accordance with an exemplary embodiment, for example, according to the configuration in which the filter 131 is arranged in the accommodation unit 110, in accordance with conditions (amount of a soft body or whether or not small-sized calculus fragments are present which are the capturing target) of the patient 600, the accommodation unit 110 including filters having respectively different pore sizes can be replaced. For example, in a case where many soft bodies and a few small-sized calculus fragments are present, an operator can correspond to the case by attaching the accommodation unit 110 including a coarse filter to the impeller holding unit 120.

In addition, according to the configuration in which the filter 131 is arranged in the accommodation unit 110, the operator can quickly use his or her manual skills by replacing the accommodation unit 110 filled with the capturing target with a new accommodation unit 110. That is, a period of time required for removing multiple capturing targets can be considerably shortened, or more capturing targets can be removed within a given period of time. For example, as in a case of transurethral ureterolithotomy (TUL), this configuration is effectively adopted when the upper limit of an operative time is regulated for critical prevention or the like from urinary duct infection after operation.

In addition, according to the configuration in which the filter 131 is arranged in the accommodation unit 110, the capturing target accommodated in the accommodation unit 110 can be removed in a state where the accommodation unit 110 is separated from the impeller holding unit 120. The impeller holding unit 120 can include the impeller 122 which is a rotating member. Accordingly, by separating the filter 131 from the impeller holding unit 120, the filter 131 can be easily cleaned, without any possibility that when the filter 131 is cleaned, the capturing target may enter a gap between the blade portions 122b of the impeller 122, a gap between the blade portion 122b and the lumen 121b of the impeller holding unit 120, or a location at which the capturing target is less likely to be removed.

In addition, according to the configuration in which the filter 131 is arranged in the accommodation unit 110, by replacing the accommodation unit 110 including the filter 131 which captures an infective capturing target, a living body can be prevented from being infected due to spreading of the capturing target.

In addition, according to the configuration in which the filter 131 is arranged in the accommodation unit 110, when a pathological examination is performed on the capturing target or the capturing target is discarded, the accommodation unit 110 accommodating the capturing target may be transported. Accordingly, it is possible to conveniently and reliably carry out handling work of the capturing target.

In addition, according to the configuration in which the filter 131 is arranged in the accommodation unit 110, the capturing target can be easily removed by arranging the accommodation unit 110 accommodating the capturing target so that the filter 131 is located above, and only by shaking the filter 131 or hitting the filter 131 against a base. In addition, a structure is adopted in which the proximal side of the filter 131 is greatly open in a state where the accommodation unit 110 is separated from the impeller holding unit 120. Accordingly, the capturing target can be easily removed by adding flowing water, for example, in a direction of the lumen 111b or the distal opening portion 111a of the accommodation unit 110 from the proximal side of the filter 131.

In addition, according to the configuration in which the filter 131 is arranged in the accommodation unit 110, the accommodation unit 110 is in a state of being detached from the impeller holding unit 120 including the impeller 122. Accordingly, there is relatively no possibility of damage to the impeller 122 when the filter 131 is cleaned. For example, even when the cleaning is performed by using those which have a thin distal end so as to remove the capturing target from the accommodation unit 110, there is no possibility of extending the thin distal end beyond the mesh of the filter 131 and damaging to the blade portion 122b of the impeller 122.

In accordance with an exemplary embodiment, according to the configuration in which the filter 131 is arranged in the impeller holding unit 120, the capturing target can be easily removed from the filter 131 exposed outward in a state where the accommodation unit 110 is separated from the impeller holding unit 120. Furthermore, after the accommodation unit 110 is detached from the impeller holding unit 120, the capturing target can be easily removed by pushing out the capturing target remaining inside the accommodation unit 110 in the axial direction.

Furthermore, in the medical device 100, the filter 131 is connected to at least any one of the proximal side of the first cylinder 111 which is included in the accommodation unit 110 and formed in a tubular shape, and the distal side of the second cylinder 121 which is included in the impeller holding unit 120 and formed in a cylindrical shape. According to this configuration, the medical device 100 can provide the filter 131 for the accommodation unit 110 and/or the impeller holding unit 120 by adopting a very simple configuration.

A medical device according to Modification Example 1 of the first embodiment will be described with reference to FIG. 11. In the medical device according to Modification Example 1 of the first embodiment, a configuration in which a shape of a first cylinder of the accommodation unit 110 is differently changed in the axial direction is different from the configuration of the medical device 100 according to the above-described first embodiment. In Modification Example 1 of the first embodiment, the same reference numerals are given to the same configuration elements as those in the above-described first embodiment, and repeated description will be omitted.

The accommodation unit 110 according to Modification Example 1 of the first embodiment will be described with reference to FIG. 11.

Figure 11:
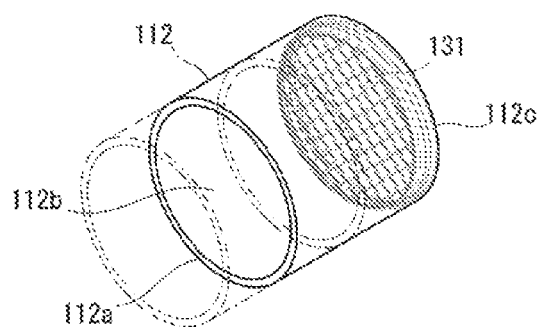
FIG. 11 is a perspective view illustrating an accommodation unit and a filter unit according to Modification Example 1 of the first embodiment.

FIG. 11 is a perspective view illustrating the accommodation unit 110 and the filter unit 130 according to Modification Example 1 of the first embodiment.

As illustrated in FIG. 11, a first cylinder 112 can be configured to optionally have a length extending along the axial direction in accordance with a size or a total amount of capturing targets which are supposed to be accommodated therein. That is, the length extending along the axial direction of the first cylinder 112 is not particularly limited as long as the first cylinder 112 can be introduced into a living body.

A medical device according to Modification Example 2 of the first embodiment will be described with reference to FIG. 12. In the medical device according to Modification Example 2 of the first embodiment, a configuration in which a shape of the first cylinder 113 of the accommodation unit 110 is differently changed between the distal side and the proximal side is different from the configuration of the medical device 100 according to the above-described first embodiment. In Modification Example 2 of the first embodiment, the same reference numerals are given to the same configuration elements as those in the above-described first embodiment, and repeated description will be omitted.

A configuration of the accommodation unit 110 according to Modification Example 2 of the first embodiment will be described with reference to FIG. 12.

Figure 12:
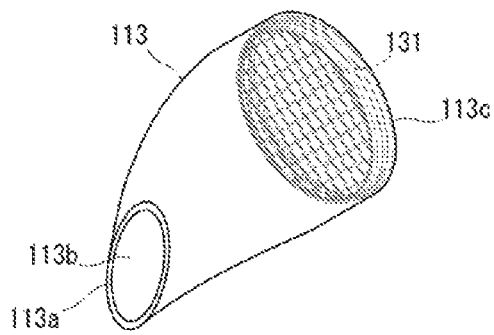
FIG. 12 is a perspective view illustrating an accommodation unit and a filter unit according to Modification Example 2 of the first embodiment.

FIG. 12 is a perspective view illustrating the accommodation unit 110 and the filter unit 130 according to Modification Example 2 of the first embodiment.

As illustrated in FIG. 12, in the first cylinder 113, an area in a cross section orthogonal to the axis along the axial direction in which a fluid of a distal opening portion 113a flows is smaller than an area in a cross section orthogonal to the axis along the axial direction in which a fluid of a proximal opening portion 113c flows. In addition, the first cylinder 113 is bent between the distal opening portion 113a and the proximal opening portion 113c. Accordingly, the lumen 113b can be smoothly formed along the axial direction.

As described above, according to the medical device of Modification Example 2 of the first embodiment, the following configurations provide an operation effect.

In the medical device, the area in the cross section orthogonal to the axis along the axial direction in which the fluid of the distal opening portion 113a flows is smaller than the area in the cross section orthogonal to the axis along the axial direction in which the fluid of the proximal opening portion 113c flows. According to this configuration, the fluid is enabled to maintain a sufficient flow rate in a region of the distal opening portion 113a (narrower than a region of the proximal opening portion 113c), and the capturing target can be sufficiently held in the region of the proximal opening portion 113c (wider than the region of the distal opening portion 113a). Furthermore, for example, when capturing the capturing target present inside a tissue lumen whose entrance is narrow, such as a small calyx, and a lower calyx, inside a living body, the thinly configured distal opening portion 113a can be inserted relatively easily into the tissue lumen. Accordingly, the distal opening portion 113a can be moved close to the capturing target.

A medical device according to Modification Example 3 of the first embodiment will be described with reference to FIG. 13. In the medical device according to Modification Example 3 of the first embodiment, a configuration in which the accommodation unit 110 is disposed at multiple locations is different from the configuration of the medical device 100 according to the above-described first embodiment. The above-described medical device 100 employs only one accommodation unit 110. In Modification Example 3 of the first embodiment, the same reference numerals are given to the same configuration elements as those in the above-described first embodiment, and repeated description will be omitted.

A configuration of the accommodation unit 110 according to Modification Example 3 of the first embodiment will be described with reference to FIG. 13.

Figure 13:
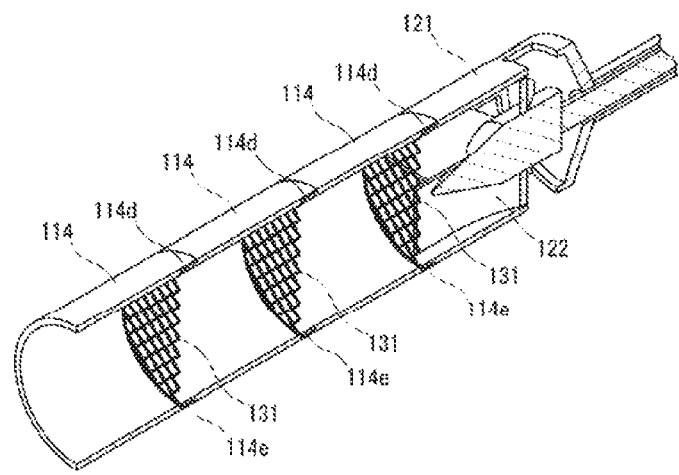
FIG. 13 is a perspective sectional view illustrating an accommodation unit, an impeller holding unit, and a filter unit according to Modification Example 3 of the first embodiment.

FIG. 13 is a perspective sectional view illustrating the accommodation unit 110, the impeller holding unit 120, and the filter unit 130 according to Modification Example 3 of the first embodiment.

A first cylinder 114 has the same configuration as that of the first cylinder 111 except that a screw thread 114e is formed on an outer peripheral surface of an end portion on the distal side (upstream side along the axial direction). The screw thread 114e adopts specifications corresponding to a screw groove 114d formed on an inner peripheral surface of an end portion on the proximal side (downstream side along the axial direction) of the first cylinder 114. That is, the screw thread 114e on the distal side of one first cylinder 114 and the screw groove 114d on the proximal side of the other first cylinder 114 are screwed to each other along the axial direction, thereby enabling the first cylinders 114 to be interlocked with each other. For example, FIG. 13 illustrates a state where three of the first cylinders 114 are interlocked with each other along the axial direction. However, the number of the first cylinders 114 is not limited.

As described above, according to the medical device of Modification Example 3 of the first embodiment, the following configurations provide an operation effect.

In the medical device, the filter 131 is arranged in the accommodation unit 110. The accommodation unit 110 is disposed at multiple locations adjacent to each other along the axial direction in which a fluid flows. According to this configuration, each time the accommodation unit 110 located on the most distal side is filled with the capturing target, only the accommodation unit 110 is detached. In this manner, an operator can quickly use his or her manual skills without a need to attach a new accommodation unit 110. That is, a period of time required for removing multiple capturing targets can be considerably shortened, or more capturing targets can be removed within a given period of time.

In addition, according to this configuration, it is possible to coarsen the mesh of the filter arranged on the uppermost stream side within multiple filters. That is, the accommodation unit 110 arranged on the uppermost stream side in the axial direction in which the fluid flows is provided with a filter having the largest pore. In this manner, the filter is used as a pre-filter. Accordingly, clogging can be prevented by sufficiently capturing the capturing target such as a semi-solid blood clot B which is relatively large-sized. A fluid or a relatively small-sized capturing target is enabled to flow to the downstream side after passing through the periphery of the blood clot B captured by the pre-filter.

A medical device 200 according to the second embodiment will be described with reference to FIGS. 14 to 16. According to the medical device 200, a configuration in which an arrangement of a first holding portion 231Ma of a first filter 231M and an arrangement of a second holding portion 231Na of a second filter 231N are different from each other is different from the configuration of the medical device 100 according to the above-described first embodiment. The above-described medical device 100 employs only one filter 131. In the second embodiment, the same reference numerals are given to the same configuration elements as those in the above-described first embodiment, and repeated description will be omitted.

A configuration of the medical device 200 according to the second embodiment will be described with reference to FIGS. 14 to 16.

Figure 14:
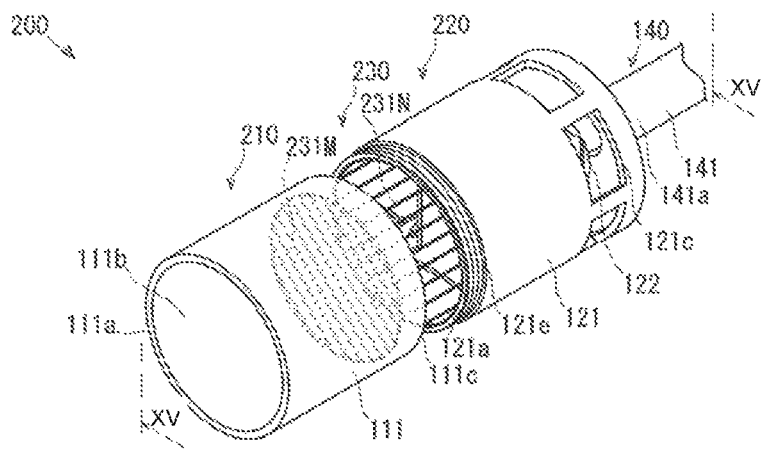
FIG. 14 is a perspective view illustrating a main unit of a medical device according to a second embodiment in a state where an accommodation unit and an impeller holding unit are separated from each other.

FIG. 14 is a perspective view illustrating a main unit of the medical device 200 according to the second embodiment in a state where an accommodation unit 210 and an impeller holding unit 220 are separated from each other. FIG. 15 is a side view in which the medical device 200 in FIG. 14 is illustrated by using a cross section taken along line XV-XV illustrated in FIG. 14. FIGS. 16A and 16 are perspective views illustrating a first filter 231M and a second filter 231N of the medical device 200 illustrated in FIG. 14. FIG. 16A is a view illustrating a state where an arrangement of a first holding portion 231Ma and an arrangement of a second holding portion 231Na are caused to coincide with each other in the circumferential direction, and FIG. 16B is a view illustrating a state where the arrangement of the first holding portion 231Ma and the arrangement of the second holding portion 231Na are caused to be different from each other in the circumferential direction.

Figure 15:
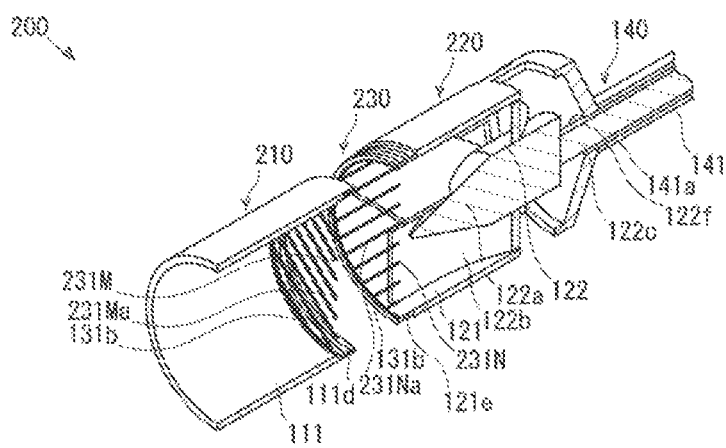
FIG. 15 is a side view in which the medical device in FIG. 14 is illustrated by using a cross section taken along line XV-XV illustrated in FIG. 14.
Figure 16A:
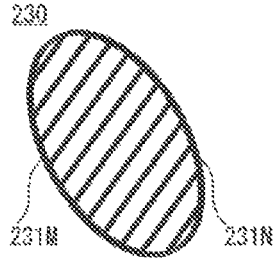
Figure 16B:
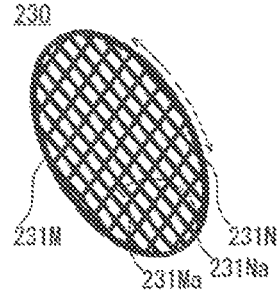

As illustrated in FIGS. 14 and 15, in the accommodation unit 210, the first filter 231M instead of the filter 131 is joined to the first cylinder 111.

As illustrated in FIGS. 14 and 15, in the impeller holding unit 220, the second filter 231N is joined to the distal side (upstream side along the axial direction) of the lumen 121b in the second cylinder 121.

As illustrated in FIGS. 14 and 15, in the filter unit 230, filters 231 are arranged one by one for the first cylinder 111 and the second cylinder 121. The filters 231 are respectively referred to as the filter 231M and the filter 231N in order to distinguishably describe the first and second filters. That is, the filter 231M and the filter 231N have the same configuration. The filter 231M can include the holding portion 231Ma and the frame portion 131b. The filter 231N can include the holding portion 231Na and the frame portion 131b. Unlike the holding portion 131a formed in a lattice shape, the holding portion 231Ma and the holding portion 231Na are formed in a palisade shape. A configuration may be adopted in which filters respectively having different intervals of the holding portion are joined one by one to the first cylinder 111 and the second cylinder 121.

As illustrated in FIG. 16A, in the filter unit 230, if the first cylinder 111 or the second cylinder 121, both of which are screwed to each other, is rotated and arranged so that a pattern of the first holding portion 231Ma of the first filter 231M and a pattern of the second holding portion 231Na of the second filter 231N overlap each other, the pores of the filter 231 become sparsest (the pores are largest).

Similarly, as illustrated in FIG. 16B, in the filter unit 230, if the first cylinder 111 or the second cylinder 121, both of which are screwed to each other, is rotated and arranged so that the pattern of the first holding portion 231Ma of the first filter 231M and the pattern of the second holding portion 231Na of the second filter 231N are orthogonal to each other, the pores of the filter 231 become densest (the pores are smallest).

As described above, according to the medical device 200 of the second embodiment, the following configurations provide an operation effect.

In the medical device 200, the filter is provided at multiple locations along the axial direction in which a fluid flows. An arrangement of the first holding portion 231Ma which holds the capturing target in the first filter 231M and an arrangement of the second holding portion 231Na which holds the capturing target in the second filter 231N are caused to be different from each other along the circumferential direction of the lumen 111b. According to this configuration, the medical device 200 can optionally adjust the density of the pores of the filter in accordance with a size of the capturing target inside the living body of the patient 600. Therefore, the medical device 200 can very efficiently capture the capturing target.

In particular, according to this configuration, when the capturing target is relatively larger than the average pore of the filter, by allowing the pores of the filter to be sparser (increasing the size of the pores), it is possible to prevent a suction force from being weakened due to clogging of the filter. In addition, when the capturing target is relatively smaller than the average pore of the filter, by allowing the pores of the filter to be denser (decreasing the size of the pores) so as to capture the capturing target, it is possible to prevent the capturing target from passing through the filter and damaging to the impeller 122.

In addition, according to this configuration, it is not necessary to prepare the multiple filters respectively having the different pore sizes in accordance with a size of the capturing target inside the living body of the patient 600. Accordingly, this configuration can be very economical. In accordance with an exemplary embodiment, for example, the inventory management can be facilitated since there is no shortage of the filter having a specific size. In addition, according to this configuration, even if the size of the capturing target inside the living body of the patient 600 varies, the density of the pores of the filter is adjusted during the operation. Accordingly, without a need to use the multiple filters respectively having the different pore sizes, the capturing target mutually having the different sizes can be captured step by step by using a single filter. Therefore, the medical device 300 can very efficiently capture the capturing target.

A medical device 300 according to the third embodiment will be described with reference to FIGS. 17 to 19. According to the medical device 300, a configuration in which a pattern of a first holding portion 331a of a first filter 331 and a pattern of a second holding portion 131a of a second filter 131 are caused to be different from each other is different from the configuration of the medical device 200 according to the above-described second embodiment. According to the above-described medical device 200, the arrangements of the holding portions 231Ma and 231Na of the filter 231 which have the same pattern are caused to be different from each other. In the third embodiment, the same reference numerals are given to the same configuration elements as those in any one of the above-described first and second embodiments, and repeated description will be omitted.

A configuration of the medical device 300 according to the third embodiment will be described with reference to FIGS. 17 and 18.

Figure 17:
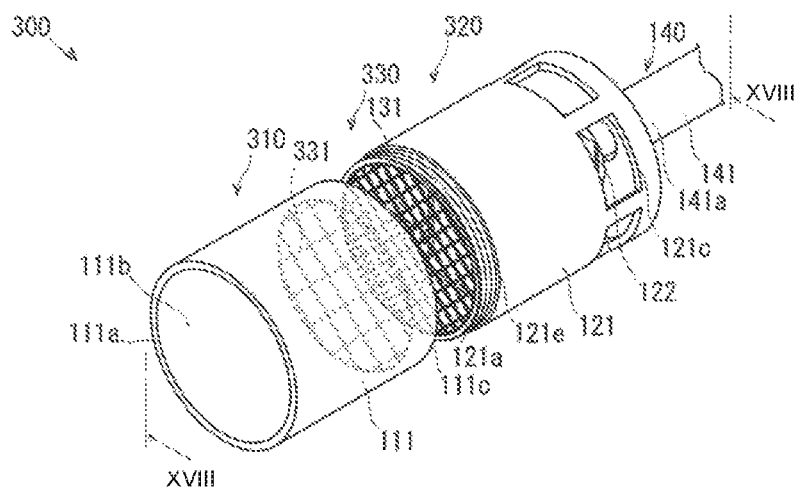
FIG. 17 is a perspective view illustrating a main unit of a medical device according to a third embodiment in a state where an accommodation unit and an impeller holding unit are separated from each other.

FIG. 17 is a perspective view illustrating a main unit of the medical device 300 according to the third embodiment in a state where an accommodation unit 310 and an impeller holding unit 320 are separated from each other. FIG. 18 is a side view in which the medical device 300 in FIG. 17 is illustrated by using a cross section taken along line XVIII-XVIII illustrated in FIG. 17.

Figure 18:
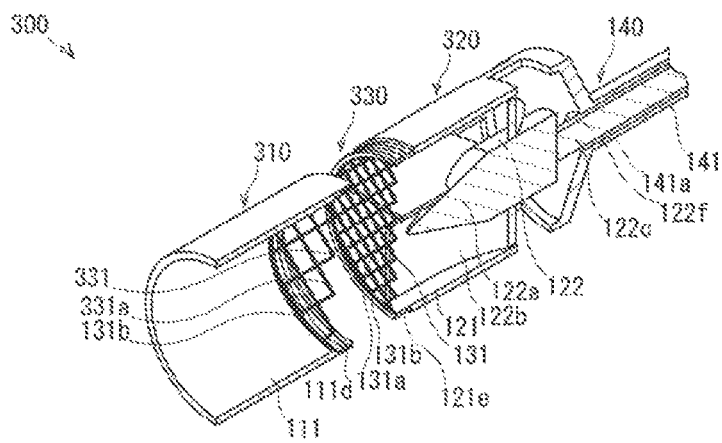
FIG. 18 is a side view in which the medical device in FIG. 17 is illustrated by using a cross section taken along line XVIII-XVIII illustrated in FIG. 17.

As illustrated in FIGS. 17 and 18, in the accommodation unit 310, the filter 331 instead of the filter 131 is arranged in the first cylinder 111.

As illustrated in FIGS. 17 and 18, in the impeller holding unit 320, the filter 131 is joined to the distal side (upstream side along the axial direction) of the lumen 121b in the second cylinder 121.

As illustrated in FIGS. 17 and 18, in the filter unit 330, the filter 331 is arranged in the first cylinder 111 of the accommodation unit 310. The filter 331 can include the holding portion 331a and the frame portion 131b. The intervals of the mesh formed in a lattice shape in the holding portion 331a are coarser than the intervals of the mesh in the holding portion 131a of the filter 131. Specifically, for example, a configuration is adopted in which the intervals of the holding portion 331a of the filter 331 are twice as coarser as the intervals of the holding portion 131a of the filter 131. In accordance with an exemplary embodiment, the filter 131 is arranged in the second cylinder 121 of the impeller holding unit 320. The holding portion 331a corresponding to the first holding portion of the filter 331 and the holding portion 131a corresponding to the second holding portion of the filter 131 are arranged separate from each other along the axial direction in which a fluid flows.

A method of using the medical device 300 according to the third embodiment will be described with reference to FIG. 19.

Figure 19:
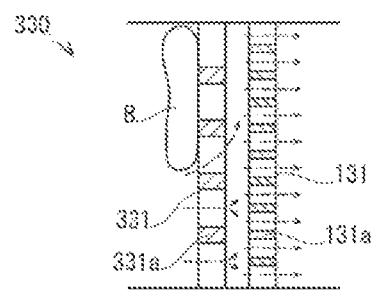
FIG. 19 is a side view schematically illustrating a state where a blood clot is captured without causing a fluid to stagnate by a first filter and a second filter of the medical device illustrated in FIG. 17.

FIG. 19 is a side view schematically illustrating a state where the blood clot B is captured while a decrease in the flow rate is minimized by the first filter 331 and the second filter 131 of the medical device 300 illustrated in FIG. 17.

The filter 331 having the relatively large pore (mesh of the holding portion is relatively coarse) between the first filter 331 and the second filter 131 is arranged on the upstream side in which a fluid flows. Furthermore, the interval between the filter 331 and the filter 131 is sufficiently lengthened so as to allow the fluid to pass therethrough. The filter 331 can be used as a pre-filter of the filter 131. That is, as illustrated in FIG. 19, a relatively big capturing target such the blood clot B, for example, can be captured by the filter 331. The fluid is enabled to flow toward the filter 131 after passing through the periphery of the blood clot B captured by the filter 331.

As described above, according to the medical device 300 of the third embodiment, the following configurations provide an operation effect.

According to the medical device 300, the filter is provided at multiple locations along the axial direction in which a fluid flows. The pattern of the first holding portion 331a which holds the capturing target in the first filter 331 and the pattern of the second holding portion 131a which holds the capturing target in the second filter 131 are caused to be different from each other. According to this configuration, even if the size of the capturing target inside the living body of the patient 600 varies, the medical device 300 can capture the capturing targets mutually having the different sizes. Therefore, the medical device 300 can very efficiently capture the capturing target.

In particular, according to this configuration, the first filter 331 can be used as a pre-filter by the filter having the larger pore (first filter 331) between the first filter 331 and the second filter 131 being arranged on the upstream side in which a fluid flows. For example, the first filter 331 sufficiently captures the capturing target such as the relatively big and semi-solid blood clot B, thereby preventing clogging. That is, the fluid is enabled to flow to the second filter 131 after passing through the periphery of the capturing target captured by the first filter 331.

In addition, according to this configuration, it is not necessary to adjust a size of the pore of the filter in accordance with a size of the capturing target inside the living body of the patient 600. Accordingly, it is possible to conveniently use the medical device 300.

Furthermore, in the medical device 300, the first holding portion 331a and the second holding portion 131a are arranged separate from each other along the axial direction in which the fluid flows. According to this configuration, the fluid does not stagnate between the first filter 331 and the second filter 131, and the fluid is enabled to quickly flow therebetween.

In accordance with an exemplary embodiment, for example, according to this configuration, the first filter 331 and the second filter 131 do not come into contact with each other. Accordingly, these filters sufficiently secure a flow path in a cross section orthogonal to the axis (sufficiently secure a sectional area), thereby enabling the fluid to smoothly flow therethrough.

A medical device 400 according to the fourth embodiment will be described with reference to FIGS. 20 to 22. According to the medical device 400, a configuration in which an operator operates the hand operation unit 150 so as to be capable of adjusting an arrangement of the first filter 331 and an arrangement of the second filter 131 inside the living body is different from the configuration of the medical device 300 according to the above-described third embodiment. In the fourth embodiment, the same reference numerals are given to the same configuration elements as those in the above-described third embodiment, and repeated description will be omitted.

A configuration of the medical device 400 according to the fourth embodiment will be described with reference to FIGS. 20 to 22B.

Figure 20:
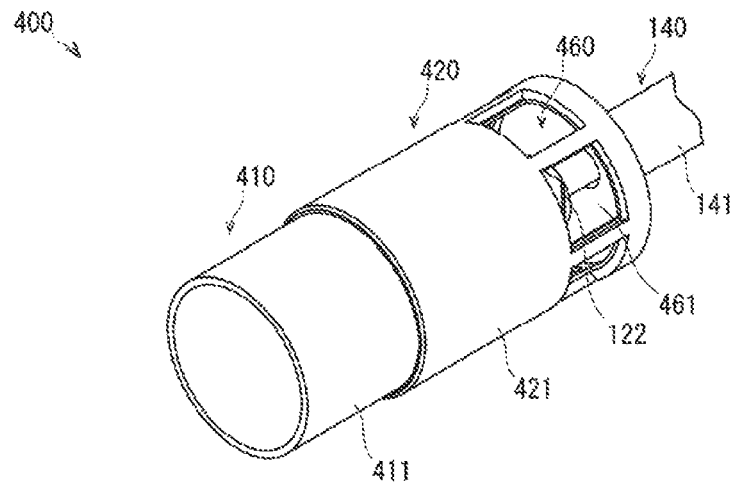
FIG. 20 is a perspective view illustrating a main unit of a medical device according to a fourth embodiment.
Figure 21:
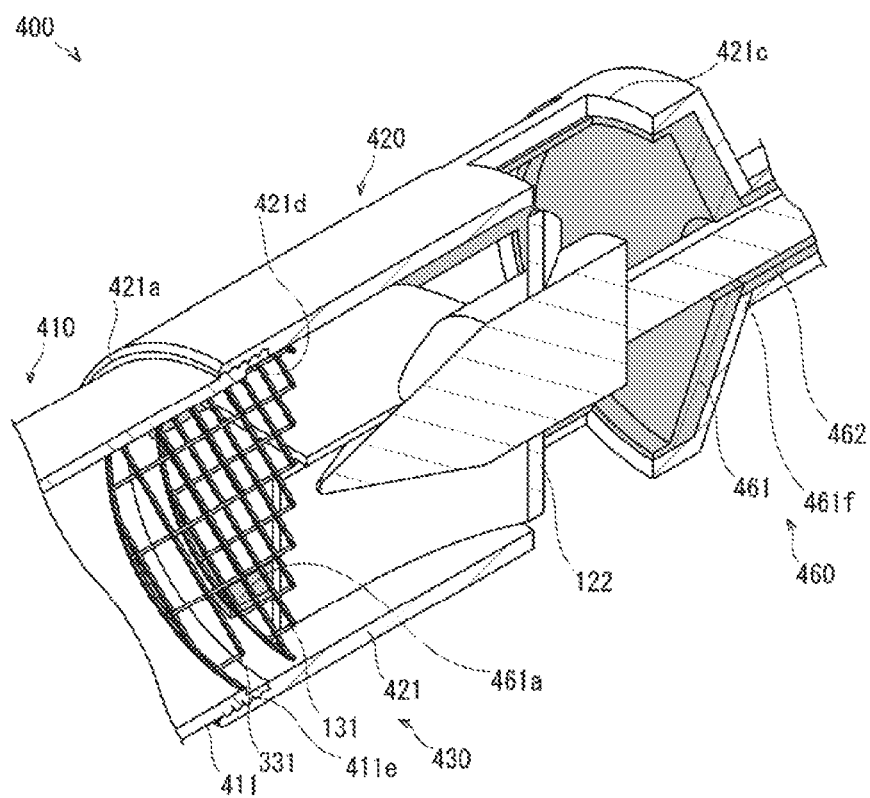
FIG. 21 is a perspective view in which the main unit of the medical device in FIG. 20 is illustrated by using an enlarged cross section.
Figure 22A:
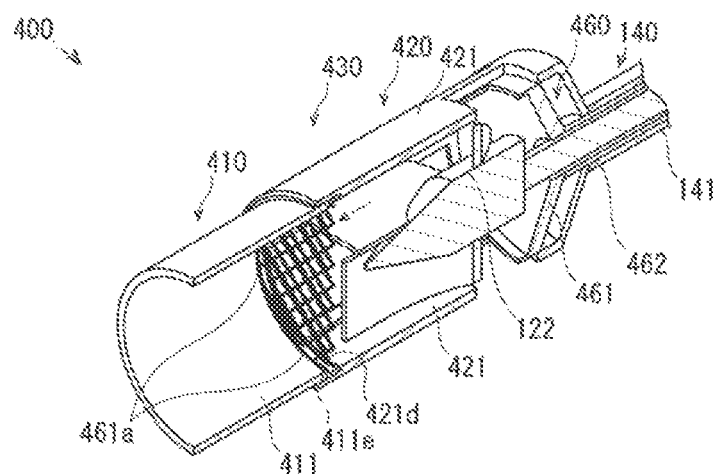
Figure 22B:
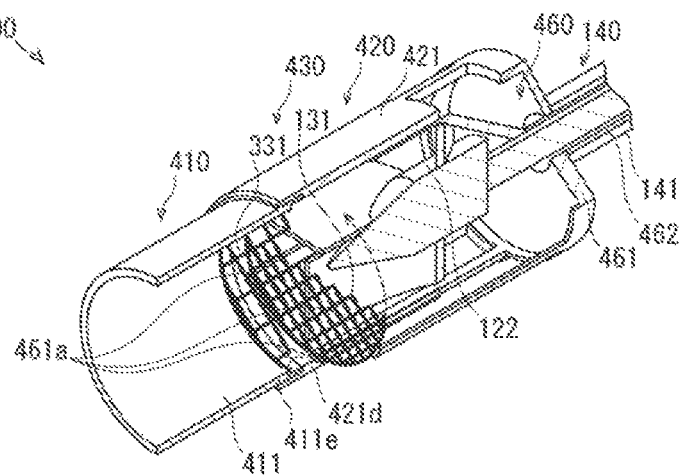

FIG. 20 is a perspective view illustrating a main unit of the medical device 400 according to the fourth embodiment. FIG. 21 is a perspective view in which the main unit of the medical device 400 in FIG. 20 is illustrated by using an enlarged cross section. FIGS. 22A and 22B are perspective sectional views illustrating the medical device 400 illustrated in FIG. 20. FIG. 22A is a view illustrating a state where an arrangement of the second filter 131 is moved along the axial direction, and FIG. 22B is a view illustrating a state where an arrangement of the second filter 131 is moved along the circumferential direction.

An accommodation unit 410 can include a first cylinder 411 instead of the first cylinder 111. As illustrated in FIGS. 20 to 22B, the first cylinder 411 has a screw thread 411e formed on an outer peripheral surface of an end portion on the proximal side (downstream side along the axial direction). Unlike the first cylinder 111, the first cylinder 411 has no screw groove 111d formed therein. The filter 331 according to the third embodiment is arranged in the first cylinder 411.

As illustrated in FIGS. 20 to 22B, an impeller holding unit 420 is configured so that a drive cylinder 461 of a drive unit 460 is rotatable along the axial direction between a second cylinder 421 and the impeller 122. Since the second cylinder 421 has the drive cylinder 461 arranged inside of the second cylinder 421, the second cylinder 421 has a shape which is formed to be one size larger radially outward than the second cylinder 121. Furthermore, the second cylinder 421 has a screw groove 421d formed on an inner peripheral surface of an end portion on the distal side (upstream side along the axial direction). The screw groove 421d of the second cylinder 421 is screwed to the screw thread 411e of the first cylinder 411.

As illustrated in FIGS. 20 to 22B, in a filter unit 430, the filter 331 according to the third embodiment is joined to the first cylinder 411 of the accommodation unit 410. In addition, as illustrated in FIGS. 20 to 22B, the filter 131 is joined to the distal side (upstream side along the axial direction) of the drive cylinder 461 of the drive unit 460. No filter is joined to the second cylinder 121 of the impeller holding unit 420.

As illustrated in FIGS. 20 to 22B, the drive unit 460 can include the drive cylinder 461 and an axle member 462. The drive cylinder 461 is formed in a tubular shape, and is arranged so as to be rotatable between the second cylinder 421 and the impeller 122 in the impeller holding unit 420. The drive cylinder 461 is formed in a cylindrical shape. The drive cylinder 461 is formed by cutting out most of the side surface along the circumferential direction so as not to inhibit a fluid from flowing in (being discharged from) the second cylinder 121. The drive cylinder 461 can include a distal opening portion 461a through which the fluid is caused to flow on the distal side (upstream side along the axial direction). The filter 131 is joined to the distal opening portion 461a. The drive cylinder 461 has a support hole 461f into which the axle portion 122c of the impeller 122 is inserted so as to be rotatable is formed at the center of an end portion on the proximal side (downstream side along the axial direction).

Similarly to the first cylinder 111, the drive cylinder 461 is configured to include a material which is transparent in a visible light region, and can adopt a configuration in which a capturing progress of the capturing target is visible from the outside. Similarly to the first cylinder 111, for example, the drive cylinder 461 can adopt a configuration in which the drive cylinder 461 contains an X-ray contrast agent and the position of the drive cylinder 461 inside the living body can be confirmed by imaging the contrast agent from the outside using X-ray fluoroscopy.

The axle member 462 is a transmission member for operating the drive cylinder 461 by using the hand operation unit 150. The axle member 462 is flexible, and is formed in an elongated cylinder shape. The distal side of the axle member 462 is connected to the center of an end portion on the proximal side (downstream side along the axial direction) of the drive cylinder 461 in a state of being rotatably inserted into the axle portion 122c of the impeller 122. The proximal side of the axle member 462 extends to the hand operation unit 150. A connector for an operator to grip is connected to the proximal side of the axle member 462.

For example, if the operator pushes the connector connected to the proximal side of the axle member 462 along the axial direction, the drive cylinder 461 is moved to the upstream side along the axial direction as illustrated in FIG. 22A. As a result, the interval along the axial direction between the filter 131 connected to the drive cylinder 461 and the filter 331 connected to the first cylinder 411 can be adjusted so as to be narrowed. In addition, for example, if an operator pulls the connector along the axial direction, the drive cylinder 461 is moved to the downstream side along the axial direction. As a result, the interval between the filter 131 and the filter 331 can be adjusted so as to be wider.

For example, if the operator rotates the connector connected to the other end of the axle member 462 along the circumferential direction, the drive cylinder 461 is rotated along the circumferential direction as illustrated in FIG. 22B. FIG. 22B illustrates a state where the drive cylinder 461 is rotated by 90° in the counterclockwise direction. Since the drive cylinder 461 is rotated along the circumferential direction, it is possible to change a pattern of the filter which can be obtained in combination between the pattern of the filter 131 connected to the drive cylinder 461 and the pattern of the filter 331 connected to the first cylinder.

As described above, according to the medical device 400 of the fourth embodiment, the following configurations provide an operation effect.

According to the medical device 400, the filter is provided at multiple locations along the axial direction in which a fluid flows. The medical device 400 has the drive unit 460 which is configured to be capable of adjusting an arrangement of the first filter 331 and an arrangement of the second filter 131 along the axial direction in which the fluid flows inside the living body and/or along the circumferential direction of the lumen 111b. According to this configuration, for example, the medical device 400 can optionally adjust the density or the interval of the pores of the filter inside the living body during the operation, in accordance with a size of the capturing target inside the living body of the patient 600. Therefore, the medical device 400 can appropriately correspond to the size of the capturing target confirmed, for example, during the operation, and can effectively capture the capturing target.

Hitherto, the medical device according to the present disclosure has been described with reference to the multiple embodiment and modification examples. However, the present disclosure can be appropriately modified, based on content described in the scope of Claims.

For example, the medical device is not limited to a form in which the medical device is introduced into the urethra 630 so as to capture and remove the capturing target, and can be introduced into other sites inside the living body so as to capture and remove the capturing target. For example, the other sites inside the living body correspond to the renal pelvis and renal calyx 640.

The detailed description above describes a medical device. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device comprising:
   an accommodation unit that includes a lumen for accommodating a capturing target present inside a living body, and a distal opening portion and a proximal opening portion which respectively communicate with the lumen;
   an impeller holding unit that includes an impeller, wherein the impeller includes a shaft portion and multiple blades, and wherein each of the multiple blades is longitudinally twisted from a distal side to a proximal side based on a rotation axis so that a rotation of the shaft portion causes a fluid to flow from the distal opening portion toward the proximal opening portion inside the living body so as to allow the lumen to aspirate the capturing target together with the fluid, and wherein the impeller holding unit is configured to be attachable to and detachable from the accommodation unit on a proximal side of the accommodation unit;
   multiple filters provided along an axial direction in which the fluid flows and configured to capture at least one or more of the capturing target, and wherein the multiple filters are arranged in the accommodation unit and/or the impeller holding unit;
   a drive unit configured to adjust an arrangement of a first filter of the multiple filters and an arrangement of a second filter of the multiple filters along the axial direction in which the fluid flows inside the living body and/or along a circumferential direction of the lumen; and
   a drive cylinder of the drive unit arranged inside of the second cylinder of the accommodation unit and configured to be rotatable between the second cylinder and the impeller in the impeller holding unit, and wherein the second filter is joined to the distal opening of the drive cylinder.

2. The medical device according to claim 1, wherein the multiple filters are connected to at least one of a proximal side of a first cylinder which is included in the accommodation unit and is formed in a cylindrical shape and a distal side of a second cylinder which is included in the impeller holding unit and is formed in a cylindrical shape.

3. The medical device according to claim 1, wherein an arrangement of a first holding portion for holding the capturing target in a first filter of the multiple filters and an arrangement of a second holding portion for holding the capturing target in a second filter of the multiple filters are different from each other along a circumferential direction of the lumen.

4. The medical device according to claim 1, wherein a pattern of the first holding portion for holding the capturing target in the first filter of the multiple filters and a pattern of the second holding portion for holding the capturing target in the second filter of the multiple filters are different from each other.

5. The medical device according to claim 3, wherein the first holding portion and the second holding portion are arranged separate from each other along the axial direction in which the fluid flows.

6. The medical device according to claim 4, wherein the first holding portion and the second holding portion are arranged separate from each other along the axial direction in which the fluid flows.

7. The medical device according to claim 1, wherein an area of the distal opening portion in a cross section orthogonal to the axis along the axial direction in which the fluid flows is smaller than an area of the proximal opening portion in a cross section orthogonal to the axis along the axial direction in which the fluid flows.

8. The medical device according to claim 1, wherein the multiple filters are arranged in the accommodation unit; and wherein the accommodation unit comprises at least two first cylinders, each first cylinder is disposed at a location adjacent to another along the axial direction in which the fluid flows.

9. A method for capturing a target present inside a living body, the method comprising:
inserting an accommodation unit into the living body, the accommodation unit including a lumen for accommodating the target present inside the living body, and a distal opening portion and a proximal opening portion which respectively communicate with the lumen;
causing a fluid to flow with an impeller holding unit that includes an impeller having a shaft portion and multiple blades, and wherein each of the multiple blades is longitudinally twisted from a distal side to a proximal side based on a rotation axis so that a rotation of the shaft portion by a motor causes the fluid to flow from the distal opening portion toward the proximal opening portion inside the living body so as to allow the lumen to aspirate the target together with the fluid, and wherein the impeller holding unit is configured to be attachable to and detachable from the accommodation unit on a proximal side of the accommodation unit;
capturing at least one or more targets with multiple filters provided along an axial direction in which the fluid flows, wherein the multiple filters are arranged in the accommodation unit and/or the impeller holding unit;
adjusting an arrangement of a first filter of the multiple filters and an arrangement of a second filter of the multiple filters along the axial direction in which the fluid flows inside the living body and/or along a circumferential direction of the lumen; and
arranging a drive cylinder of the drive unit inside of the second cylinder of the accommodation unit and configured to be rotatable between the second cylinder and the impeller in the impeller holding unit, and wherein the second filter is joined to the distal opening of the drive cylinder.

10. The method according to claim 9, comprising:
connecting the multiple filters to at least one of a proximal side of a first cylinder which is included in the accommodation unit and is formed in a cylindrical shape and a distal side of a second cylinder which is included in the impeller holding unit and is formed in a cylindrical shape.

11. The method according to claim 9, wherein an arrangement of a first holding portion for holding the target in a first filter of the multiple filters and an arrangement of a second holding portion for holding the target in a second filter of the multiple filters are different from each other along a circumferential direction of the lumen.

12. The method according to claim 9, wherein a pattern of the first holding portion for holding the target in the first filter of the multiple filters and a pattern of the second holding portion for holding the target in the second filter of the multiple filters are different from each other.

13. The method according to claim 11, comprising:
arranging the first holding portion and the second holding portion to be separate from each other along the axial direction in which the fluid flows.

14. The method according to claim 12, comprising:
arranging the first holding portion and the second holding portion to be separate from each other along the axial direction in which the fluid flows.

15. The method according to claim 9, wherein an area of the distal opening portion in a cross section orthogonal to the axis along the axial direction in which the fluid flows is smaller than an area of the proximal opening portion in a cross section orthogonal to the axis along the axial direction in which the fluid flows.

16. The method according to claim 9, comprising:
arranging the multiple filters in the accommodation unit; and
the accommodation unit comprises at least two first cylinders, disposing each first cylinder of the accommodation unit at a location adjacent to another along the axial direction in which the fluid flows.

17. The medical device according to claim 1, further comprising:
a motor configured to rotate an axle portion, which is connected to the shaft portion of the impeller.

18. A medical device comprising:
an accommodation unit that includes a lumen for accommodating a capturing target present inside a living body, and a distal opening portion and a proximal opening portion which respectively communicate with the lumen;
an impeller holding unit that includes an impeller, wherein the impeller includes a shaft portion and multiple blades, and wherein each of the multiple blades is longitudinally twisted from a distal side to a proximal side based on a rotation axis so that a rotation of the shaft portion causes a fluid to flow from the distal opening portion toward the proximal opening portion inside the living body so as to allow the lumen to aspirate the capturing target together with the fluid;

multiple filters provided along an axial direction in which the fluid flows and configured to capture at least one or more of the capturing target, and wherein the multiple filters are arranged in the accommodation unit and/or the impeller holding unit;

a drive unit configured to adjust an arrangement of a first filter of the multiple filters and an arrangement of a second filter of the multiple filters along the axial direction in which the fluid flows inside the living body and/or along a circumferential direction of the lumen; and a drive cylinder of the drive unit arranged inside of the second cylinder of the accommodation unit and configured to be rotatable between the second cylinder and the impeller in the impeller holding unit, and wherein the second filter is joined to the distal opening of the drive cylinder.

* * * * *